United States Patent [19]

Hoffmann-Paquotte

[11] 4,255,584

[45] Mar. 10, 1981

[54] METHOD FOR PREPARING 5-CYANO-4-METHYL-OXAZOLE

[75] Inventor: Hans Hoffmann-Paquotte, Inzlingen, Fed. Rep. of Germany

[73] Assignee: Hoffman-La Roche Inc., Nutley, N.J.

[21] Appl. No.: 89,757

[22] Filed: Oct. 30, 1979

[30] Foreign Application Priority Data

Nov. 2, 1978 [DE] Fed. Rep. of Germany ....... 2847625
Aug. 9, 1979 [CH] Switzerland ......................... 7309/79

[51] Int. Cl.³ .......................................... C07D 263/36
[52] U.S. Cl. .................................................. 548/236
[58] Field of Search ..................... 548/236; 260/465 B

[56] References Cited

U.S. PATENT DOCUMENTS

| | | | |
|---|---|---|---|
| 3,222,374 | 12/1965 | Chase | 548/236 |
| 4,011,234 | 3/1977 | Paquotte | 548/236 |
| 4,026,901 | 5/1977 | Coffen | 548/236 |

FOREIGN PATENT DOCUMENTS 532938  2/1941  United Kingdom .
1081838  9/1967  United Kingdom .

*Primary Examiner*—Anton H. Sutto
*Attorney, Agent, or Firm*—Jon S. Saxe; George M. Gould; John B. Wilson

[57] ABSTRACT

The present invention encompasses a method for preparing 5-cyano-4-methyl-oxazole, comprising reacting 5-carbamoyl-4-methyl-oxazole with a lower alkanecarboxylic acid anhydride in the presence of a nickel or copper catalyst. The product, 5-cyano-4-methyl-oxazole, is an intermediate in the synthesis of vitamin $B_6$.

10 Claims, No Drawings

METHOD FOR PREPARING 5-CYANO-4-METHYL-OXAZOLE

BACKGROUND OF INVENTION

The present invention relates to a method for preparing an oxazole. More particularly, the invention is concerned with a novel method for preparing 5-cyano-4-methyl-oxazole which is an important intermediate in the manufacture of Vitamin $B_6$.

Heretofore, 5-cyano-4-methyl-oxazole has been obtained by reacting 5-carbamoyl-4-methyl-oxazole with phosphorus pentoxide heated to fusion temperature. However, various disadvantages are associated with this process. In particular, the yield is relatively low. An improvement in this process consists in carrying out the reaction of phosphorus pentoxide with 5-carbamoyl-4-methyl-oxazole in the presence of a solvent, namely quinoline. This improved process, has, however, the disadvantage that quinoline is insufficiently stable under the reaction conditions, has a disagreeable odour and is noxious. Further, the procedure for regenerating the quinoline and for working-up the product resulting from the phosphorus pentoxide to an environmentally acceptable product is expensive and encumbered with a series of technological problems. Moreover, not only quinoline but also phosphorus pentoxide is expensive and commercially scarce.

Another improvement in the manufacture of 5-cyano-4-methyl-oxazole consists in reacting 5carbamoyl-4-methyl-oxazole with a lower alkanecarboxylic acid anhydride and subjecting the reaction mixture or the 5-[N-(lower alkanoyl)-carbamoyl]-4-methyl-oxazole isolated from the latter to a pyrolysis. This pyrolytic process has certain disadvantages such as, in particular, high working temperatures, great problems with the materials from which the reactor may be constructed and formation of byproducts which are difficult to recycle.

DESCRIPTION OF THE INVENTION

The present invention reacts 5-carbamoyl-4-methyl-oxazole with a lower alkanecarboxylic acid anhydride in the presence of a nickel or copper catalyst to provide 5-cyano-4-methyl-oxazole.

The present invention enables 5-cyano-4-methyl-oxazole to be manufactured in a simple and inexpensive manner starting from inexpensive and readily accessible raw materials, while avoiding the disadvantages of the known processes described above and affording the desired 5-cyano-4-methyl-oxazole in high yield and good quality.

Lower alkanecarboxylic acid anhydrides which are preferred are the symmetrical or mixed anhydrides of straight-chain or branched-chain alkanecarboxylic acids containing from 1 to 7-carbon atoms. Examples of such anhydrides are acetic anhydride, propionic acid anhydride, isopropionic acid anhydride, butyric acid anhydride, n-valeric acid anhydride, the mixed anhydride of formic acid and acetic acid and the like. Symmetrical lower alkanecarboxylic acid anhydrides, especially the symmetrical anhydrides of alkanecarboxylic acids containing from 1 to 5 carbon atoms, are preferably used. Acetic anhydride is especially preferred.

In carrying out this invention, any nickel or copper material conventionally employed as a catalyst may be utilized. The nickel or copper catalyst can be not only metallic nickel or copper but also nickel or copper compounds, especially Ni(II) or Cu(II) compounds such as the carbonates, particularly basic carbonates, oxides, hydroxides, halides, more particularly the chlorides, formates, acetates and the like. Catalysts which have a good solubility in the reaction medium are preferred, with nickel acetate and copper acetate being especially preferred as catalysts. The reaction medium is the solvent in which the present invention takes place to produce 5-cyano-4-methyl-oxazole. The medium preferred is the lower alkanecarboxylic acid anhydride in excess, with acetic anhydride in excess being especially preferred.

The reaction of 5-carbamoyl-4-methyl-oxazole with a lower alkanecarboxylic acid anhydride is conveniently carried out using about a 3 to 10 molar excess of anhydride over the 5-carbamoyl-4-methyl-oxazole compound. The reaction is preferably carried out, however, using about 3 to 7 molar excess and especially preferably using a 4 or 5 molar excess of anhydride.

Further, the reaction is conveniently carried out at an elevated temperature with the boiling point of the reaction mixture being the preferred elevated temperature. In order to prevent a back-reaction at the elevated temperature between the alkanecarboxylic acid formed during the reaction and the end product formed, it is also convenient to remove continously from the reaction mixture the alkanecarboxylic acid being formed during the reaction. There are conventional art known procedures for removing the alkanecarboxylic acid from the reaction mixture, which procedures may be employed by this invention. This removal is preferrably effected by carrying out the reaction at the boiling point of the reaction, distilling off the alkanecarboxylic acid formed together with excess anhydride and 5-cyano-4-methyl-oxazole formed and immediately cooling the distillate. The 5-cyano-4-methyl-oxazole, the end product, can be isolated by fractional distillation from the distillate. Further amounts of end product can be isolated from the residue of the reaction. This is conveniently carried out by cleaving the 5-[N-(lower alkanoyl)-carbamoyl]-4-methyl-oxazole, which is obtained as the byproduct, with methanol and reacting the resulting 5-carbamoyl-4-methyl-oxazole in the manner previously described.

The process provided by the present invention can be carried out continuously or batch-wise. It is preferably carried out continously.

In accordance with a preferred embodiment of the process provided by the invention, 5-carbamoyl-4-methyl-oxazole is reacted with a 5-molar excess of acetic anhydride with the addition of 0.01 mol of nickel acetate as the catalyst at the boiling point of the mixture. After rapid distillation, the distillate is cooled.

The following Examples, in which all percentages are percentages by weight, illustrate the present invention and are not intended to limit the invention in scope or spirit.

EXAMPLE I 128 g [1 molar (1 mol)] of 98.5% 5-carbamoyl-4-methyl-oxazole-(1,3), 510.5 g (5 mol) of acetic anhydride and 1.8 g (0.01 mol) of nickel acetate were placed in a 1 liter three-necked flask provided with a stirrer, thermometer and distillation bridge. The batch was heated with a heating apparatus (450 watt) as rapidly as possible (about 12 minutes). At an internal temperature of 120°–125° C. the solution became clear and at a sump temperature (temperature inside the flask) of 136°-137° C. and a head temperature of 131°-132° C. the solution began to boil. The contents of the flask were distilled within 20 minutes until the sump temperature reached 160° C. The heating source was then removed and the rest of the distillate was distilled off by slowly evacuating the apparatus by means of a water-jet vacuum. At the end of the distillation the residue still present in the flask was again heated to a sump temperature of 100° C. using an oil bath of 100° C. There were obtained 626.4 g of a colourless distillate and 14.2 g of a light brown residue. The amount of 5-cyano-4-methyl-oxazole present in the distillate amounted to 15.8%, corresponding to 99.0 g. This corresponds to a chemical yield in the distillate of 91.5% based on 5-carbamoyl-4-methyl-oxazole used.

EXAMPLE II

A further 13 batches were processed in an analogous manner to that described in Example I. The results are summarized in the following Table in which CMO is an abbreviation of 5-cyano-4-methyl-oxazole.

The total yield of 5-cyano-4-methyl-oxazole in the distillate of the 14 batches thus amounted to 1363.7 g. This corresponds to a chemical yield of 97.0% of theory.

Example IV 128 g (1 mol) of 98.5% 5-carbamoyl-4-methyl-oxazole, 510.5 g (5 mol) of acetic anhydride and 2 g (0.01 mol) of copper acetate monohydrate in a 1 liter three-necked flask, provided with a stirrer, thermometer and distillation bridge, were heated with a 450 watt heating apparatus as rapidly as possible (about 12 minutes). At an internal temperature of 120°-125° C. the solution became clear and grass-green in colour. At a sump temperature of 138° C. and a head temperature of 132° C. the solution began to boil. The contents of the flask were distilled within 20 minutes until the sump temperature reached 160° C. The heating source was then removed and the rest of the distillate was distilled off by slowly evacuating the apparatus up to the complete water-jet vacuum. At the end of the distillation the residue still present in the flask was again heated to a sump temperature of 100° C. with an oil bath of 100° C.

TABLE I

| Experiment No. | 1 | 2 | 3 | 4 | 5 | 6 | 7 | 8 | 9 | 10 | 11 | 12 | 13 | 1-13 |
|---|---|---|---|---|---|---|---|---|---|---|---|---|---|---|
| Distillate (g) | 625.7 | 626.0 | 627.1 | 626.0 | 626.8 | 626.8 | 626.5 | 626.0 | 625.9 | 626.2 | 626.3 | 626.5 | 626.8 | 8.142.6 |
| CMO content (%) | 15.7 | 15.55 | 15.6 | 15.7 | 15.95 | 16.05 | 15.85 | 15.85 | 16.2 | 16.25 | 15.75 | 15.8 | 15.9 | 15.8+ |
| CMO yield (g) | 98.2 | 97.3 | 97.8 | 98.3 | 100.0 | 100.6 | 99.3 | 99.2 | 101.4 | 101.8 | 98.6 | 99.0 | 99.7 | 1.286.5 |
| Chemical yield % | 90.8 | 90.0 | 90.5 | 90.9 | 92.5 | 93.0 | 91.9 | 91.8 | 93.8 | 94.2 | 91.2 | 91.6 | 92.2 | 91.5 |
| Residue (g) | 14.7 | 14.8 | 13.5 | 14.8 | 14.1 | 13.8 | 14.2 | 14.9 | 14.0 | 13.8 | 13.8 | 14.1 | 14.3 | 184.8 |

+Average of 3 analyses (15.9; 15.8; 15.7)

The chemical yield thus amounted, after the analysis of the combined distillates from 13 similar batches, to 91.5% of theory [based on 5-carbamoyl-4-methyl-oxazole used].

Example III

The residue of each individual batch from Example II was treated with 170 ml of methanol and boiled under reflux for 10 minutes. Thereby, the 5-(N-acetyl-carbamoyl)-4-methyl-oxazole present in the residue decomposed quantitatively with the reformation of 5-carbamoyl-4-methyl-oxazole and the formation of methyl acetate.

The pooled, methanol treated and dissolved residues were concentrated, first at normal pressure and then to dryness in a water-jet vacuum. The yield amounted to 145.5 g, corresponding to 78.7% of the amount used.

The foregoing 145.5 g were reacted with 510.5 g of acetic anhydride and 1.8 g of nickel acetate in an analogous manner to that described in Example I. There were obtained 603.2 g of distillate containing 12.8% (corresponding to 77.2 g) of 5-cyano-4-methyl-oxazole.

There were obtained 614.3 g of a colourless distillate and 25.4 g of a brown-black residue. The amount of 5-cyano-4-methyl-oxazole present in the distillate amounted to 14.4%, corresponding to 88.5 g. This corresponds to a chemical yield of 81.9% based on 5-carbamoyl-4-methyl-oxazole used.

Example V

The following experiments using various catalysts were carried out in an analogous manner to that described in Example I. The results are summarised in Table II.

Batch:
126.1 g (1 mol) of 5-carbamoyl-4-methyl-oxazole
510.5 g (5 mol) of acetic anhydride;
+0.01 mol of catalyst.

TABLE II

| Experiment No. | Catalyst | Distillation residue (g) | Distillate g | Distillate % CMO | Distillate g CMO | Yield CMO % |
|---|---|---|---|---|---|---|
| 1 | Ni(OAc)$_2$ . 2H$_2$O | 2.5 | 13.4 | 625.3 | 15.85 | 99.1 | 99.7 |
| 2 | NiCO$_3$ . 2NiOH . 4H$_2$O | 1.3* | 16.4 | 620.7 | 15.30 | 95.0 | 87.9 |
| 3 | NiO | 0.7 | 18.6 | 619.4 | 15.25 | 94.5 | 87.4 |
| 4 | Ni(COOH)$_2$ . 2H$_2$O | 1.9 | 21.0 | 616.1 | 15.0 | 92.4 | 85.5 |

*1/300 mol used here, since 3 Ni$^{++}$/mol catalyst

I claim:

1. A method for preparing 5-cyano-4-methyl-oxazole, comprising: reacting 5-carbamoyl-4-methyl-oxazole with a lower alkanecarboxylic acid anhydride in the presence of a nickel or copper catalyst to produce 5-cyano-4-methyl oxazole.

2. A method according to claim 1 wherein the lower alkanecarboxylic acid anhydride is acetic anhydride.

3. A method according to claim 1 wherein the lower alkanecarboxylic acid anhydride is about 3 to 10 molar excess of the 5-carbamoyl-4-methyl-oxazole.

4. A method according to claim 1 wherein the catalyst is Ni(II) or Cu(II) compounds.

5. A method according to claim 1 wherein the catalyst is nickel acetate or copper acetate.

6. A method according to claim 1 wherein said anhydride is a reaction medium for reacting the 5-carbamoyl-4-methyl-oxazole with said anhydride in the presence of the catalyst.

7. A method according to claim 6 wherein the catalyst has good solubility in the reaction medium.

8. A method according to claim 6 wherein 5-carbamoyl-4-methyl-oxazole reacts with the anhydride in the presence of the catalyst at the boiling point of the reaction mixture and the mixture is continuously distilled at said boiling point to provide a distillate containing 5-cyano-4-methyl-oxazole.

9. A method according to claim 8 wherein the distillate is fractional distilled to provide 5-cyano-4-methyl-oxazole.

10. A method according to claim 1 wherein the reaction is carried out continuously.

* * * * *